United States Patent
Orphanos

(10) Patent No.: US 11,642,474 B2
(45) Date of Patent: May 9, 2023

(54) SURGICAL INSUFFLATION AND IRRIGATION CONDUITS AND METHODS FOR USE

(71) Applicant: Saphena Medical, Inc., West Bridgewater, MA (US)

(72) Inventor: Mark J. Orphanos, Foxboro, MA (US)

(73) Assignee: Saphena Medical, Inc., West Bridgewater, MA (US)

( * ) Notice: Subject to any disclaimer, the term of this patent is extended or adjusted under 35 U.S.C. 154(b) by 870 days.

(21) Appl. No.: 16/575,882

(22) Filed: Sep. 19, 2019

(65) Prior Publication Data

US 2020/0094001 A1 Mar. 26, 2020

Related U.S. Application Data

(60) Provisional application No. 62/734,660, filed on Sep. 21, 2018.

(51) Int. Cl.
| | |
|---|---|
| *A61M 13/00* | (2006.01) |
| *A61B 17/32* | (2006.01) |
| *H01B 9/02* | (2006.01) |
| *H01B 7/00* | (2006.01) |
| *A61M 3/02* | (2006.01) |
| *A61B 17/00* | (2006.01) |

(52) U.S. Cl.
CPC ... *A61M 13/003* (2013.01); *A61B 17/320016* (2013.01); *A61M 3/02* (2013.01); *H01B 7/0072* (2013.01); *H01B 9/02* (2013.01); *A61B 2017/00778* (2013.01); *A61B 2217/007* (2013.01); *H01B 7/00* (2013.01)

(58) Field of Classification Search
CPC .. H02G 3/0456; F16L 3/2235; A61M 13/003; A61M 3/02; A61B 17/320016; A61B 2017/00778; A61B 2217/007; H01B 7/0072; H01B 9/02
See application file for complete search history.

(56) References Cited

U.S. PATENT DOCUMENTS

| | | | |
|---|---|---|---|
| 2,910,524 | A | 10/1959 | Schaffhauser |
| 4,357,940 | A | 11/1982 | Muller |
| 4,704,091 | A * | 11/1987 | Owens ............... H01R 13/465 439/282 |
| 5,399,159 | A | 3/1995 | Chin et al. |
| 5,414,212 | A * | 5/1995 | Clouet ............... H01B 7/0045 174/36 |

(Continued)

FOREIGN PATENT DOCUMENTS

| | | |
|---|---|---|
| DE | 202019100208 U1 | 1/2019 |
| WO | 2013044128 A1 | 3/2013 |
| WO | WO-2013044128 A1 * | 3/2013 ............... G02B 6/04 |

OTHER PUBLICATIONS

International Search Report in International Application No. PCT/US2019/051953 dated Nov. 19, 2019.

*Primary Examiner* — Pete T Lee
(74) *Attorney, Agent, or Firm* — Greenberg Traurig, LLP; Chinh H. Pham; Joshua I. Rudawitz

(57) ABSTRACT

The presently disclosed embodiments relate to insufflation and irrigation conduits for vessel harvesting systems and methods of their use. In particular, the present disclosure relates to a system having a combined cabling for providing gases, liquids, and/or electrical power to an attached medical device and method of use.

7 Claims, 9 Drawing Sheets

(56) References Cited

U.S. PATENT DOCUMENTS

| | | | |
|---|---|---|---|
| 5,454,791 A | | 10/1995 | Tovey et al. |
| 5,587,736 A | | 12/1996 | Walls |
| 8,792,760 B2 | * | 7/2014 | Choi ................... G02B 6/441 |
| | | | 385/101 |
| 9,119,900 B2 | | 9/2015 | Chin |
| 9,283,045 B2 | | 3/2016 | Rhee et al. |
| 9,498,246 B2 | | 11/2016 | Chin et al. |
| 9,814,481 B2 | | 11/2017 | Orphanos et al. |
| 9,943,328 B2 | | 4/2018 | Orphanos et al. |
| 10,201,382 B2 | * | 2/2019 | Wiener ............. A61B 18/1206 |
| 2003/0032916 A1 | * | 2/2003 | Rowe .................... A61M 37/00 |
| | | | 604/20 |
| 2003/0181917 A1 | | 9/2003 | Gertner |
| 2004/0133228 A1 | | 7/2004 | Bayer |
| 2005/0065511 A1 | | 3/2005 | Geistert |
| 2005/0159764 A1 | | 7/2005 | Kasahara |
| 2006/0074444 A1 | | 4/2006 | Lin et al. |
| 2010/0122844 A1 | * | 5/2010 | Efraimsson ............ G02B 6/483 |
| | | | 174/70 C |
| 2010/0292533 A1 | | 11/2010 | Kasahara et al. |
| 2013/0197299 A1 | | 8/2013 | Chin |
| 2015/0133924 A1 | | 5/2015 | McLawhorn et al. |
| 2015/0217102 A1 | | 8/2015 | Bourgeois et al. |
| 2015/0237770 A1 | * | 8/2015 | Yamasaki ............ H02G 3/0412 |
| | | | 174/68.3 |
| 2016/0286697 A1 | * | 9/2016 | Degen ...................... H01R 4/10 |
| 2017/0332884 A1 | | 11/2017 | Amling et al. |
| 2018/0042694 A1 | | 2/2018 | Kadykowski |
| 2019/0192188 A1 | | 6/2019 | Orphanos et al. |

\* cited by examiner

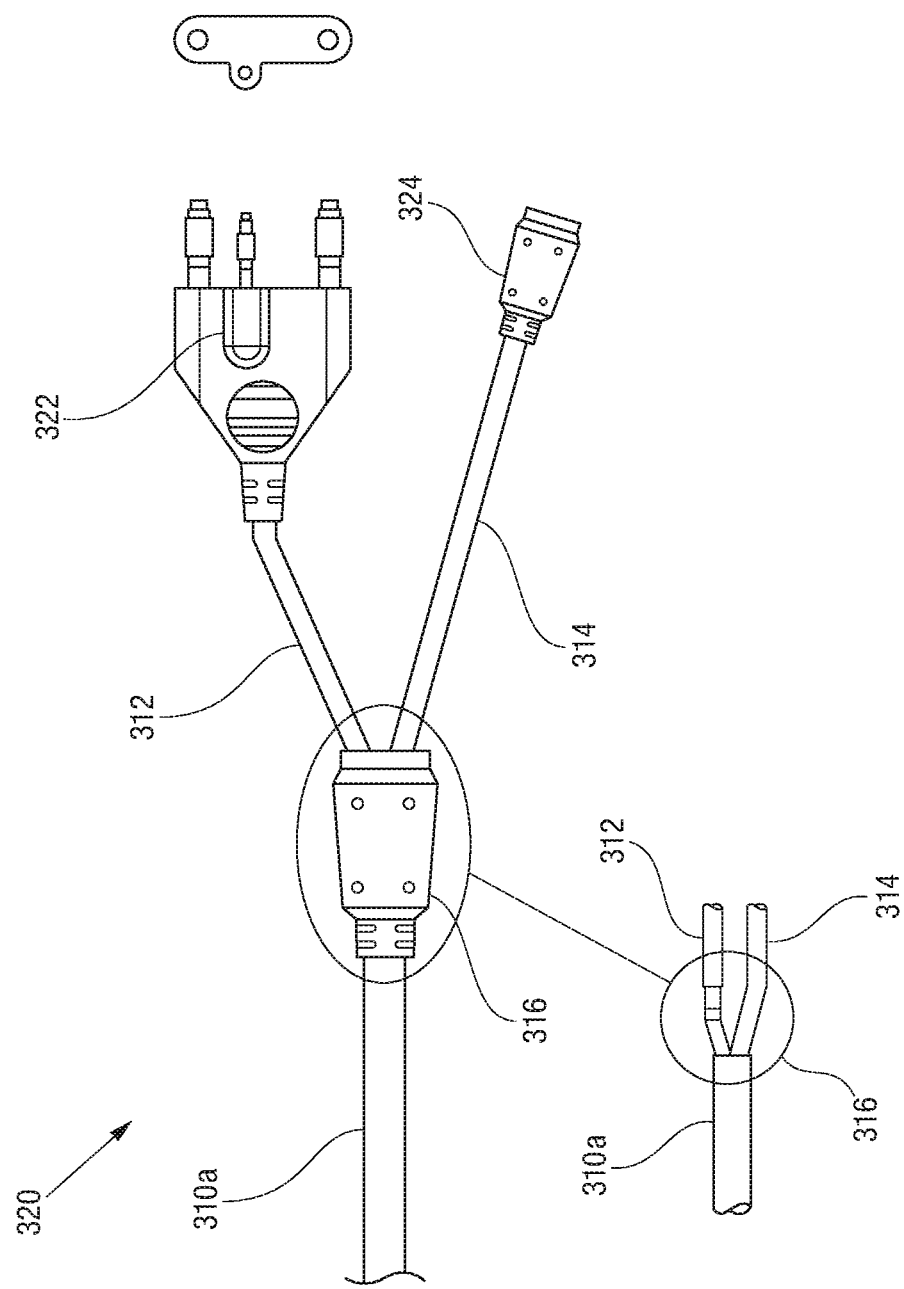

SURGICAL INSUFFLATION AND IRRIGATION CONDUITS AND METHODS FOR USE

CROSS-REFERENCE TO RELATED APPLICATION(S)

This application claims priority to, and the benefit of, U.S. Provisional Application No. 62/734,660, filed Sep. 21, 2018, for all subject matter common to both applications. The disclosure of said provisional application is hereby incorporated by reference in its entirety.

FIELD OF THE INVENTION

The presently disclosed embodiments relate to insufflation and irrigation conduits for vessel harvesting systems and methods of their use. In particular, the present disclosure relates to a system having a combined cabling for providing gases, liquids, and/or electrical power to an attached medical device and method of use.

BACKGROUND

Generally, surgical devices, such as devices for vessel harvesting, will require the use of multiple tools each including dedicated wiring or tubing for each particular function. As such, the surgical area can be disorganized and over encumbered by the various devices, wiring, and cables when performing a surgical procedure. In one example, vessel harvesting is a surgical technique that is commonly used in conjunction with coronary artery bypass surgery. During a bypass surgery, blood is rerouted to bypass blocked arteries to restore and improve blood flow and oxygen to the heart. The blood may be rerouted using a bypass graft, where one end of the by-pass graft is attached to a blood source upstream of the blocked area and the other end is attached downstream of the blocked area, creating a "conduit" channel or new blood flow connection bypassing the blocked area. Commonly, a surgeon will remove or "harvest" healthy blood vessels from another part of the body to create the bypass graft. The success of coronary artery bypass graft surgery may be influenced by the quality of the conduit and how it is handled or treated during the vessel harvest and preparation steps prior to grafting.

Vessel harvesting methods involve selecting a vessel, traditionally, the great saphenous vein in the leg or the radial artery in the arm to be used as a bypass conduit sealing off and cutting smaller blood vessels that branch off the main vessel conduit and harvesting the main conduit from the body. This practice does not harm the remaining blood vessel network, which heals and maintains sufficient blood flow to the extremities, allowing the patient to return to normal function without noticeable effects.

A minimally invasive technique for vessel harvesting is known as endoscopic vessel harvesting ("EVH"), a procedure that requires only small incisions. During EVH and similar surgical procedures, media are insufflated or injected into the patient's leg cavity to expand the leg cavity and provide a good visual field inside the leg cavity or flush tissue or components. The media is provided in the operating room ("OR") and delivered via a flexible tube to the sterile field.

Some EVH devices have small lengths of tubing extending from their bodies at the handle with which the operator (e.g., surgeon, physician assistant) can connect this OR tube. The connection can be included on the flexible trocar of the EVH device. In all cases, the OR tube must be present in the sterile field and is attached to the EVH system at or near the handle of the device, where the operator's hands are, atop the OR table. Also, all EVH devices have a power cable to deliver energy to the patient (see, e.g., FIG. 1). This power cable is connected to the EVH device at or near its handle, which again is atop the OR table in the sterile field. The power cable extends approximately 10 feet or so to an OR-supplied generator, typically on a cart (outside of the sterile field).

The foregoing arrangement for performing an EVH procedure in a typical OR setting is illustrated in FIG. 2. In such conventional configurations there are many tubes, wires, and instruments that clutter the OR table and the sterile field, thereby impeding the progress of the operator (e.g., surgeon, physician assistant). Frequently the tubing and wires become entangled as the EVH device is rotated during a normal EVH procedure. It is therefore advantageous to remove as many tubes and wires as possible from this area, to minimize the clutter in the sterile field and simplify the EVH procedure. Such OR table and sterile field cluttering and the resulting entanglement and related difficulties are also present in other types of laparoscopic and endoscopic surgical procedures.

SUMMARY

There is a need for improvements for how medical devices are connected to equipment supplying those devices with gases, liquids, power, etc. within an operating environment. The present disclosure provides, in various embodiments solutions to address this need, in addition to having other desirable characteristics.

In accordance with example embodiments of the present invention, a cabling apparatus is provided. The cabling includes electrical wiring for delivering power, a lumen for delivering media, and a cable shielding surrounding both the electrical wiring and the lumen.

In accordance with aspects of the present invention, the cabling further includes an electrical plug coupled to a proximal end of the electrical wiring. The cabling can further include a lumen connection coupled to a proximal end of the lumen. The cabling can further include a bifurcation splitting the cable shielding at a proximal end of the cabling apparatus. The cabling can further include a molded strain relief at a distal end of the cabling apparatus for coupling to a medical device. The electrical wiring can include three wires. The cabling can further include at least one spacer within the cabling.

In accordance with example embodiments of the present invention, a system is provided. The system includes a device body, cabling operationally engaging at least the body, electrical wiring formed at least partially within the cabling, and a lumen formed at least partially within the cabling.

In accordance with aspects of the present invention, the system includes device body is an endoscopic vessel harvesting device. The lumen can be an insufflation pathway for providing insufflation gas for delivery by the surgical device. The lumen can be an irrigation pathway for providing irrigation for delivery by the surgical device. The electrical wiring can be a power cable for the surgical device.

In accordance with example embodiments of the present invention, a method for delivering media to a patient's body part in a sterile field is provided. The method include providing a surgical device having electrical wiring and a lumen formed at least partially within a single cabling, the single cabling having a proximal end located outside of the sterile field and a distal end located inside of the sterile field, operably connecting the proximal end of the lumen to a media supply located outside the sterile field, and delivering media from the media supply through the lumen to the patient's body part through the distal end of the single cabling.

In accordance with aspects of the present invention, the method is performed during an endoscopic vessel harvesting procedure. The media delivering step can include insufflating the patient's body part. The media delivering step can include irrigating the patient's body part.

BRIEF DESCRIPTION OF DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 4A illustrates an example diagrammatic side view of a proximal end of an insufflation conduit of the present disclosure, as incorporated into a power cable of an EVH device, in accordance with the present disclosure.

DETAILED DESCRIPTION

Figure 1:
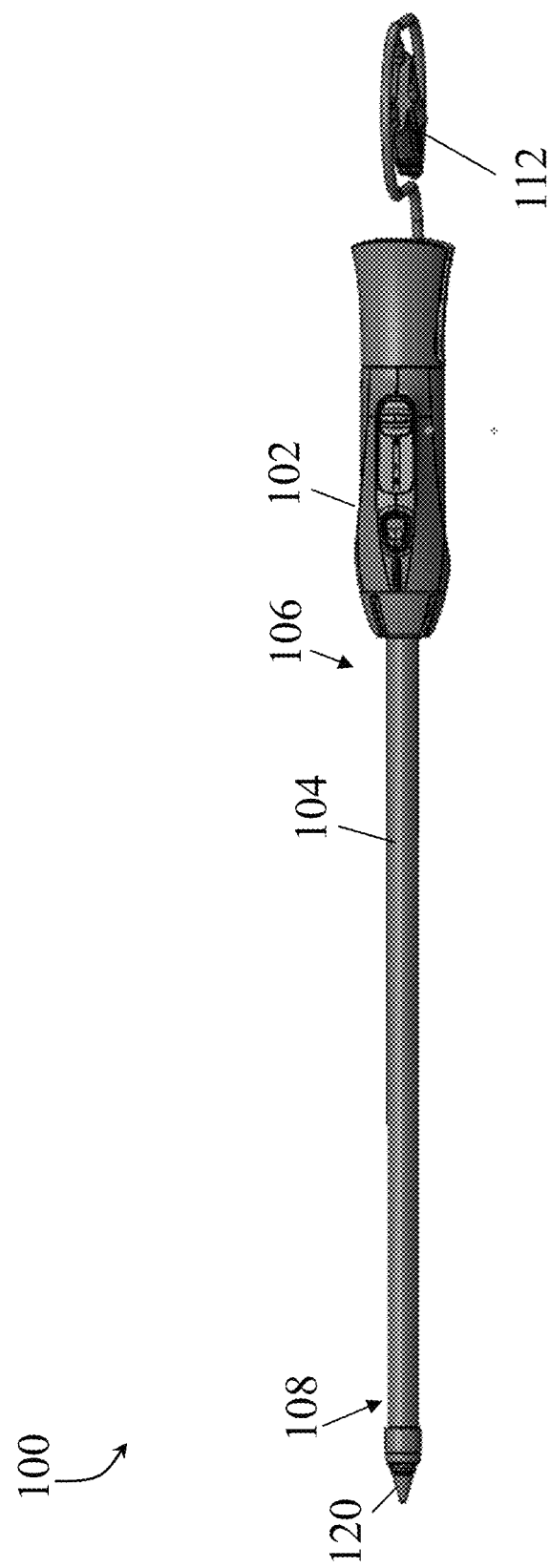
FIG. 1 illustrates an example EVH device and its power cable.

An illustrative embodiment of the present disclosure relates to a device combining electrical wiring and a fluid transferring channel within a single shielded housing for use by one or more surgical or medical devices. Specifically, the present disclosure relates to systems and methods for creating and using a combined cord used for surgical or medical devices, for example, providing power, insufflation, and irrigation conduits for an endoscopic vessel harvesting (EVH) device. Some embodiments of the present disclosure include a surgical device, for example, an EVH device. The surgical device can include a body, a cable operationally engaging at least the body, and a conduit formed at least partially within the cable. The conduit may be for insufflation or irrigation. In some embodiments, the power cabling and insufflation conduits can be combined into a single structure for providing power and delivering media (i.e., fluids such as gases (e.g., $CO_2$) or liquids (e.g., saline)) during a surgical procedure while minimizing clutter in the sterile field and on the OR table, to ultimately simplify the procedure. In other words, the power cable of the surgical device can be designed to include a media delivery lumen therein using the single cabling structure. Power can be delivered to the surgical device while media can be delivered to the patient via the delivery lumen. In some embodiments, the power cable of the EVH device can be configured to include a space sufficient to deliver the media without the presence of an additional delivery lumen.

In some embodiments of the present disclosure include a method for delivering media to a body of a patient within a sterile field using the system of the present disclosure. The method can include steps for (a) providing a surgical device having a cable and a conduit formed at least partially within a single cable, the conduit having a proximal end located outside of the sterile field and a distal end located inside of the sterile field, (b) operably connecting the proximal end of the conduit to a media supply tube outside the sterile field, and (c) delivering media from the media supply lumen to the patient's body part through the distal end of the conduit. The method can be performed during different types of operations, including an endoscopic vessel harvesting EVH procedure. The method can be used to deliver different combinations of gases and liquids to a body of the patient, for example, insufflating the patient's body part and/or irrigating the patient's body part.

FIGS. 1 through 5C wherein like parts are designated by like reference numerals throughout, illustrate an example embodiment or embodiments of improved operation for medical devices requiring multiple wired, tubular, etc. connections, according to the present disclosure. Although the present disclosure will be described with reference to the example embodiment or embodiments illustrated in the figures, it should be understood that many alternative forms can embody the present disclosure. One of skill in the art will additionally appreciate different ways to alter the parameters of the embodiment(s) disclosed, such as the size, shape, or type of elements or materials, in a manner still in keeping with the spirit and scope of the present disclosure.

Referring to FIG. 1, an exemplary vessel harvesting device 100 in accordance with the present disclosure is depicted. The device 100, in some embodiments, can include housing 102 which can be configured to house the various components of the device 100, including internal wiring to receive and deliver power to said components, and communicate data to systems outside of the housing 102. The housing 102 can also include buttons, switches, etc. for controlling operation of the device 100. For example, the housing 102 can include a button for powering a cutting component of the device 100. The housing 102 can be constructed from any combination of materials utilizing any combination of systems and methods known in the art. For example, the housing 102 can be constructed from a biocompatible material, such as, plastic material, elastomeric material, metallic material, shape memory material, composite material or any other materials that has the desired characteristics. In some embodiments, the device 100 and components thereof can be disposable.

In some embodiments, the housing 102 may be coupled to external wires or cabling 112 that are configured for providing power and transferring data with the device 100 and the subsystems thereof. As would be appreciated by one skilled in the art, the cable 112 can also be configured to provide power to other systems known in the art, for example, a cutting sub-system of the device 100, such as the cutting systems discussed with respect to U.S. Pat. Nos. 9,119,900, 9,498,246, 9,814,481, and 9,943,328 and, all incorporated herein by reference. The cable 112 can provide a combination of wiring for different power and data cabling within a singular shield or can be a combination of wires braided together into a single line.

Figure 2:
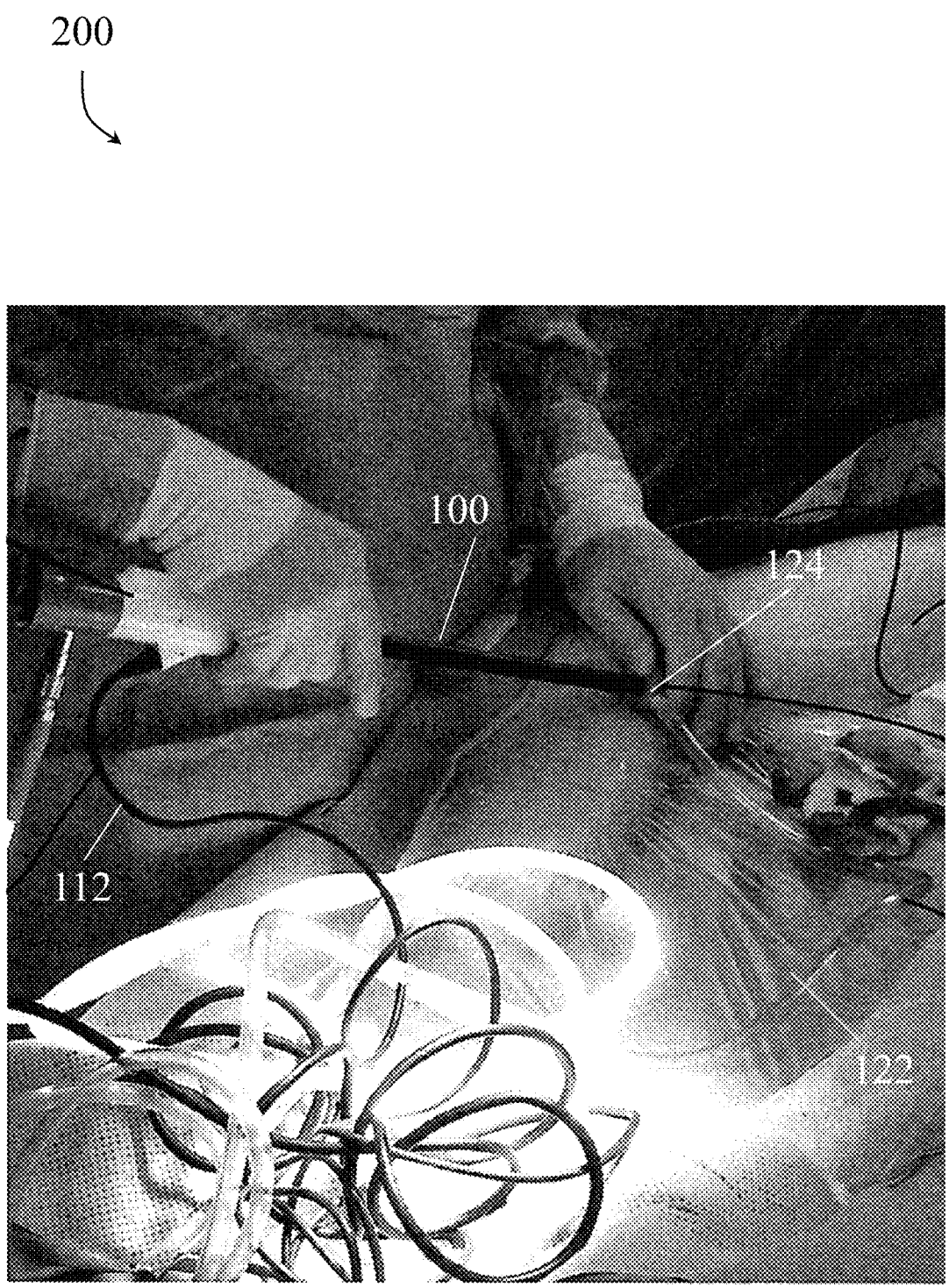
FIG. 2 illustrates an example EVH procedure in a conventional OR setting, where the EVH system includes many tubes, wires, and instruments.

Reference is made to FIG. 2, which illustrates an operator using an existing EVH system 200 in an EVH procedure for operation within an OR. The EVH system 200 can include an EVH device 100 having a power cable 112 attached thereto. The EVH system 200 can also include multiple other tubes and wires, including a clear tube 122 that terminates/forms a connection at a trocar portion 124 of the EVH device 100. The clear tube 122 is the media delivery tube provided by the OR. In some embodiments of the disclosed device and method (as discussed below), the EVH system is modified such that the media delivery tube 122 is integrated into the power cable 112, whereby the media connection is formed at the generator, 5-10 feet away (not shown) instead of at the trocar portion 124, as shown in FIG. 2. The media delivery tube 16 is thereby be removed from the sterile field, reducing clutter in the sterile field and on the OR table, and simplifying the EVH procedure.

Continuing with reference to FIGS. 1 and 2, in some embodiments, the device 100 can include an elongated body 104 that can be configured for passing extravascular through an entry incision to a vessel harvesting site and configured to introduce media from one or more tubes 122 to the incision site. To aid in navigating the elongated body 104 to a site of harvesting, the elongated body 104 may be sufficiently rigid axially along its length. To provide the elongated body 104 with such characteristic, in an embodiment, the elongated body 104 may be made from a biocompatible material, such as, plastic material, elastomeric material, metallic material, shape memory material, composite material or any other materials that has the desired characteristics. To the extent desired, the elongated body 104 may be provided with some flexibility to move radially or laterally from side to side depending on the application.

In some embodiments, an elongated body 104 can extend longitudinally from the distal end of the housing 102. The elongated body 104 can be substantially solid or hollow and have a proximal end 106 and a distal end 108. The proximal end 106 can be coupled to and/or within the housing 102 using any combination of coupling mechanisms. In some embodiments, the elongated body 104 can include an inner cavity extending from the proximal end 106 to the distal end 108 to enable transmission of media from the canister trocar portion 124 or other connection point. As would be appreciated by one skilled in the art, the elongated body 104 can house and/or be coupled to a variety of other tools or components, for example, a cutting tool.

In some embodiments, the device 100 may include one or more lumen with lumen that accommodate advancing instruments, wires, or materials therethrough. In some embodiments, the device 100 may include a conduit through which wires or cabling may be advanced for powering and/or communicating with electrical components within the device 100. Similarly, the device 100 can include a conduit for transmission of media from the trocar portion 124 or other connection point to a desired destination. The conduit for transmission of the media can be shared with the other components or can be an isolated separate conduit exiting out the tip 120 of the device 100.

In some embodiments, elongated body 104 can terminate at a dissection tip 120 or can have a dissection tip 120 coupled to the distal end 108 of the elongated body 104. In some embodiments, the dissection tip 120 may include a generally tapered section which terminates in a generally blunt end for atraumatic separation of a vessel segment, being harvested from surrounding tissue, while minimizing or preventing tearing or puncturing of nearby vessels or tissue as the device 100 is navigated along a vessel segment. Although illustrated as being blunt, it should of course be understood that, to the extent desired, the end of the dissection tip 120 may be made relatively pointed to enhance advancement of the distal end of the device 100. Similarly, the tapered section may be configured differently structurally, so as to enhance the operability of the device 100.

In some embodiments, to reduce likelihood of trauma during a dissection process, in some embodiments, the dissection tip 120 may be radially pliable, flexible or deformable so that the dissection tip may deflect slightly under exertion of force applied to the dissection tip 120. In some embodiments, the dissection tip 120 is radially compressible so that the walls of the dissection tip 120 can deform under exertion of force normal to the tip surface. To that end, the dissection tip 120 may be formed from thin wall plastic material to enable the dissection tip to flex under load. Suitable materials include, but are not limited to, polycarbonate, polyethylene terephthalate glycol-modified (PETG), polyethylene terephthalate (PET) and other materials that provide enough optical clarity while allowing the dissection tip to flex under load. At the same time, the dissection tip 120 may be provided with sufficient column strength in the axial or longitudinal direction to allow dissection of the vessel from the surrounding connective tissue. Other characteristics of the dissection tip 120 are contemplated, such as having variable strengths: (1) in an axial direction versus a longitudinal direction, wherein the axial strength is greater than the longitudinal strength; (2) in a longitudinal direction versus an axial direction, wherein the longitudinal strength is greater than the axial strength; or (3) the axial direction versus a longitudinal direction, wherein the axial strength is approximate the longitudinal strength. It is also possible that the dissection tip 120 may include two or more materials, wherein at least one material can have different material properties, such as elasticity, hardness, tensile strength.

In some embodiments, the EVH device 100 of the present disclosure can be used to provide a gas/fluid media independent from a remote tank(s) and/or using external tubing 122 during a procedure. For example, the EVH device 100 of the present disclosure can be used to provide $CO_2$ from canisters during a vessel harvesting procedure. When using the EVH device 100 during an operation, the user would first make an incision at a desired location as normal. The user can also implement a tip search or cut down method if desirable. In some embodiments, the user can utilize sealing device 200, such as a gas pad, to create a seal between the patient and the EVH device 100. For example, a user can use a gas seal pad such as the gas seal pad discussed in U.S. patent application Ser. No. 16/225,049, incorporated herein by reference. With the elongated body 104 and/or gas pad in place and insufflation is ready to begin, the user can engage the release of the media from the canister(s), via the tubes 122. For example, the media can be released under pressure by activating a mechanism/button on the housing 102. At this point the internal canister(s) will release the stored media (e.g., $CO_2$) into the patient. A mechanism internal to the EVH device 100 can control the pressure and flow rate of the media delivered from the canister. If the user would like to remove the EVH device 100 or otherwise stop flow/pressure, the user can disengage the release or pressure through the same mechanism/button on the handle.

Figure 3:
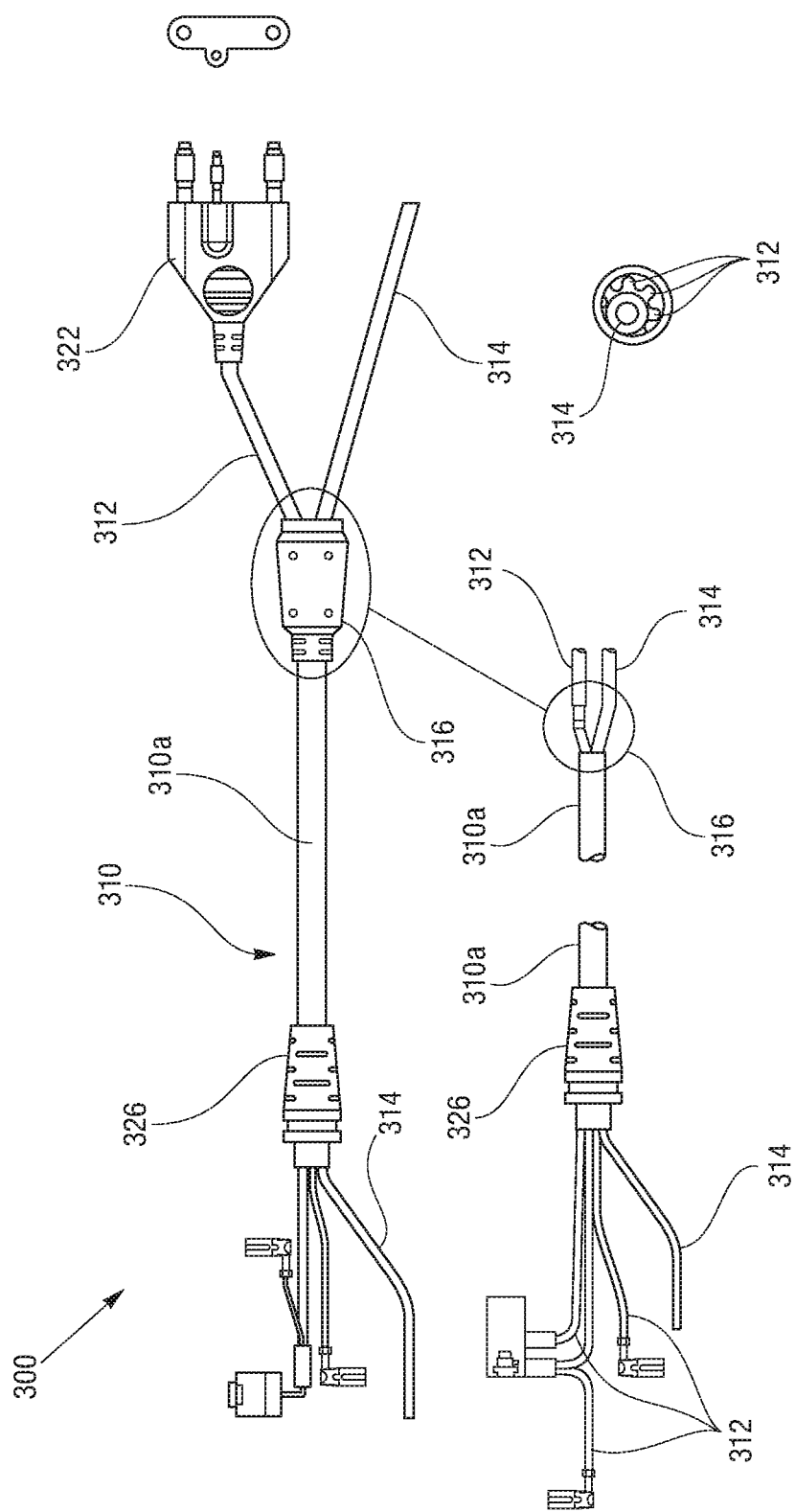
FIG. 3 illustrates an example diagrammatic side view of an insufflation conduit of the present disclosure, as incorporated into a power cable of an EVH device, in accordance with the present disclosure.

Referring to FIG. 3, in some embodiments, a system 300 is provided to deliver power, signals, gas, liquid, and/or lighting through a single combined cabling structure 310. FIG. 3 illustrates a cabling 310 for delivering a combination of power, signals, gases, liquids, and/or lighting to a medical device, for example, the EVH device 100. The cabling 310 can be designed to safely encase a combination of wiring, lumens, and conduits for the power, signals, gases, liquids and/or lighting to be delivered over a single line instead of having multiple cables with separate cables for each utility (e.g., power, signals, insufflation, lighting, etc.), such as depicted in FIG. 2. The cabling 310 can be sized and shaped to encase all the wiring and conduits while also remaining flexible for ease of movement by an operator.

In some embodiments, the cabling 310 can include or otherwise house an electrical wiring 312 for conveying a combination of power from a power source (not shown), signals to/from a processing unit or other circuitry, and a media delivery lumen 314 for conveying a media (e.g., $CO_2$, flushing, etc.) from a medium container or reservoir (not shown). The electrical wiring 312 can include any combination of wire types, made from any combination of conductive materials, in any range of gauges, etc. In some embodiments, the cabling 310 can include a bifurcation 316 junction where the media delivery lumen 314 and the electrical wiring 312 separate for attachment to their respective source devices. The cabling 310 can further include a distal end 318 opposite the bifurcation 316 with a length of the cabling 310*a* (e.g., a flexible elongated body) extending therebetween. The distal end 318 can include the wiring and conduit connectors needed to be coupled to a medical device (e.g., EVH device 100) secured within the EVH device (not shown).

Referring to FIG. 4A, an example view of the proximal end 320 of the cabling 310 is depicted. The proximal end 320 of the power cable can be located at an opposing end of the cabling 310 from the device 100 attached thereto (i.e., the generator end, or proximal end). In some embodiments, the proximal end 310 can include the bifurcation 316, an electrical plug 322, and a lumen connection 324 for coupling to respective power sources and gas/liquid sources. The electrical plug 322 and the lumen connection 324 can include any combination of coupling mechanism typically found in an operating room. For example, the electrical plug 322 can be a three prong plug and the lumen connection 324 can be a Luer connector.

In some embodiments, the electrical wiring 312 can be coupled to the electrical plug 322 and can extend to and/or is coupled to the bifurcation 316. Similarly, the lumen 314 can be coupled to a lumen connection 324 and can extend to and/or is coupled to the bifurcation 316. The bifurcation 316 is the junction point for the separate wiring 312 and the lumen 314 combining to form a single cabling along the length of cabling 310*a*. In some embodiments, the bifurcation 316 can be designed to be located proximate an OR generator, which is typically 5-10 feet away from the sterile field/OR table, where the OR media supply lumen would connect (i.e., away from the sterile field). In such a configuration, an operator (e.g., surgeon, physician assistant) can make the media connection via the lumen connection 324 from the OR supply and a power connection via the electrical plug 322 at the generator, outside of the sterile field (e.g., about 5-10 feet away). In other words, the bifurcation 316 provides a y-type connection combining the electrical wiring 312 and the lumen 314 into the single length of cabling 310*a* for use within a sterile field and extending to the medical device 100.

Figure 4B:
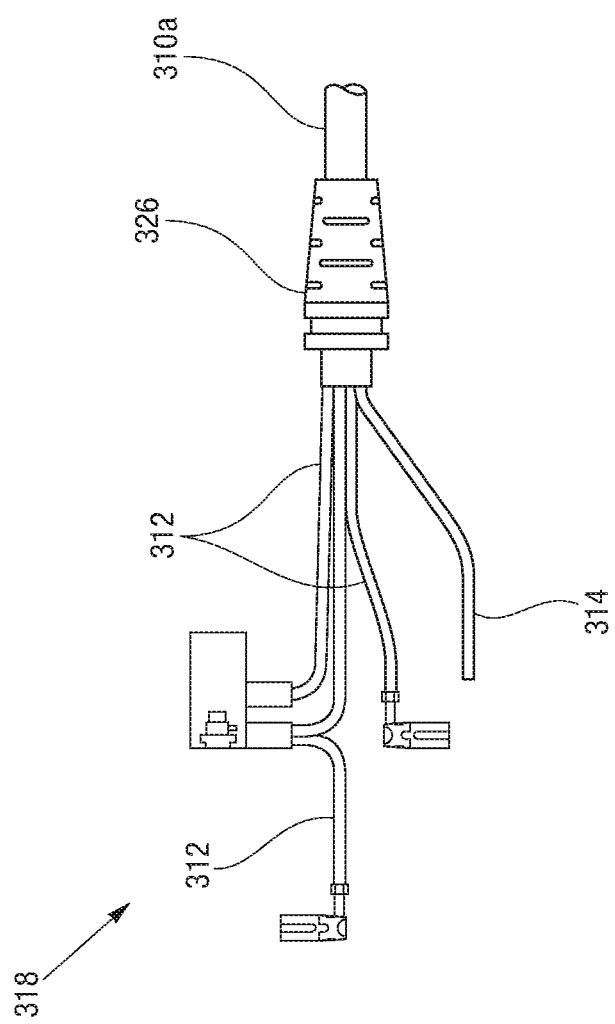
FIG. 4B illustrates an example diagrammatic side view of a distal end of an insufflation conduit of the present disclosure, as incorporated into a power cable of an EVH device, in accordance with the present disclosure.

Referring to FIG. 4B, an example view of the distal end 318 of the cabling 310 is depicted. The distal end 118 of the power cable can be located at the end of the cabling 310 that is coupled to the medical device 100. In some embodiments, the distal end 318 can include the end of the length of cabling 310*a* and can include a molded strain relief 326 coupled to the distal end of the length of cabling 310*a*. The molded strain relief 326 can be designed to provide a sealed connection between the end of the length of cabling 310*a* and an opening within a housing of the device 100. The molded strain relief 326 can also provide the flexibility for the device 100 and the cabling 310 to move freely without risk of damaging the coupling point of the two.

In some embodiments, the electrical wiring 312 and the lumen 314 can extend beyond the length of cabling 310*a* and the molded strain relief 326 to be connected to their respective termination points within the housing of the device 100. For example, the electrical wiring 312 can be connected to the electrical system of the device 100 and the lumen 314 can be connected to the dispersion mechanism of the device 100. In other words, the electrical wiring 312 and the lumen 314 can exit the cabling 310 to the inside the body of the device 100, with its termination points hidden from view of the user. With the ends of the electrical wiring 312 and lumens 314 located within the device body, they can be coupled to various components of the device for their respective uses. For example, the electrical wiring 312 can be directly soldered to their leads, tab connectors, circuit boards, etc. to provide a combination of power and signals for use by the attached device. In some embodiments, the lumen 314 can exit the cabling 310 to a position within of the body of the device 100. Regardless of the configuration, the appropriate connections of the electrical wiring 312 and the lumen 314 can be made by the device manufacturer (i.e., during fabrication of the device), and not by the operator of the device (e.g., the surgeon, physician assistant).

In some embodiments, the electrical wiring 312 can include multiple electrical wires with various electrical connectors. In one example, the electrical wiring 312 can include three wires including a hot wire, a neutral wire, and a ground wire. Each of the wires can be coupled to the appropriate termination points within the device 100. For example, referring to FIG. 4B, one wire can be connected to ground, one to power, and at least two wires can be connected to an activation switch for the device 100. In some embodiments, the lumen 314 can feed into the body of the device 100 and can be designed to provide the device 100 with gas and/or liquid for delivery from the device. For example, the lumen 314 can be used by a EVH device to provide insufflation. In some embodiments, the lumen 314 can include a filter at a distal end opening of the lumen 314, to block particulate matter in the media from inadvertently being delivered to the patient, potentially causing serious injury or death.

Figure 5A:
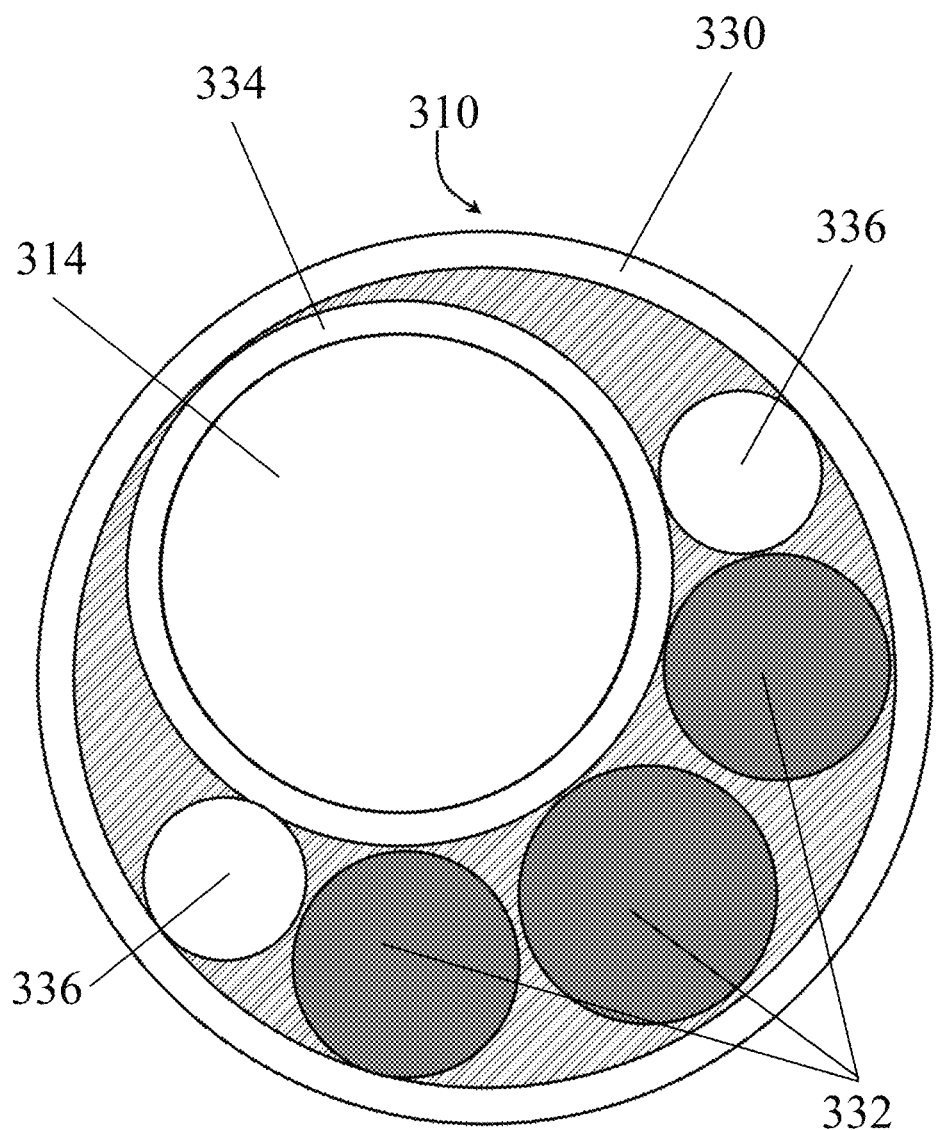
FIGS. 5A, 5B, 5C, and 5D illustrate example cross-sectional views of an insufflation conduit of the present disclosure, as incorporated into a power cable of an EVH device, in accordance with the present disclosure, and While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.
Figure 5B:
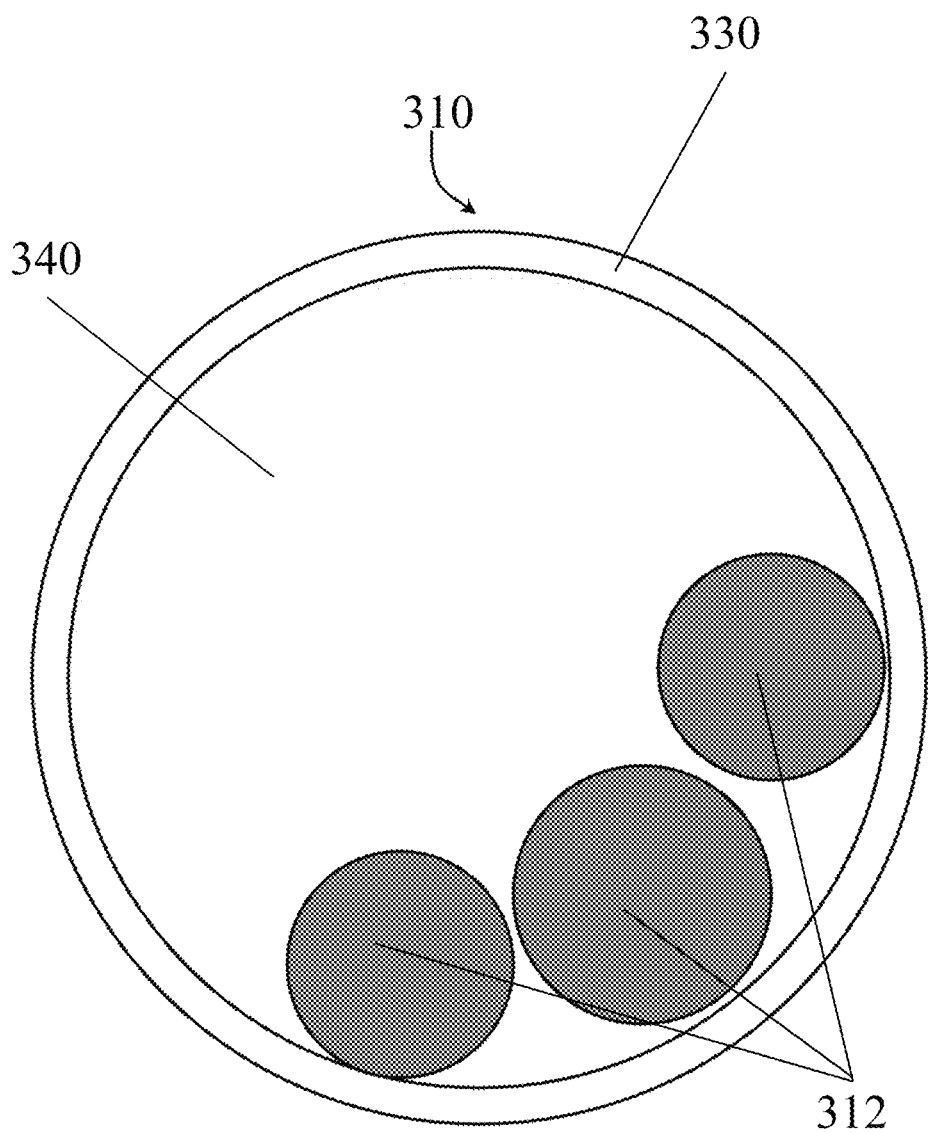
Figure 5C:
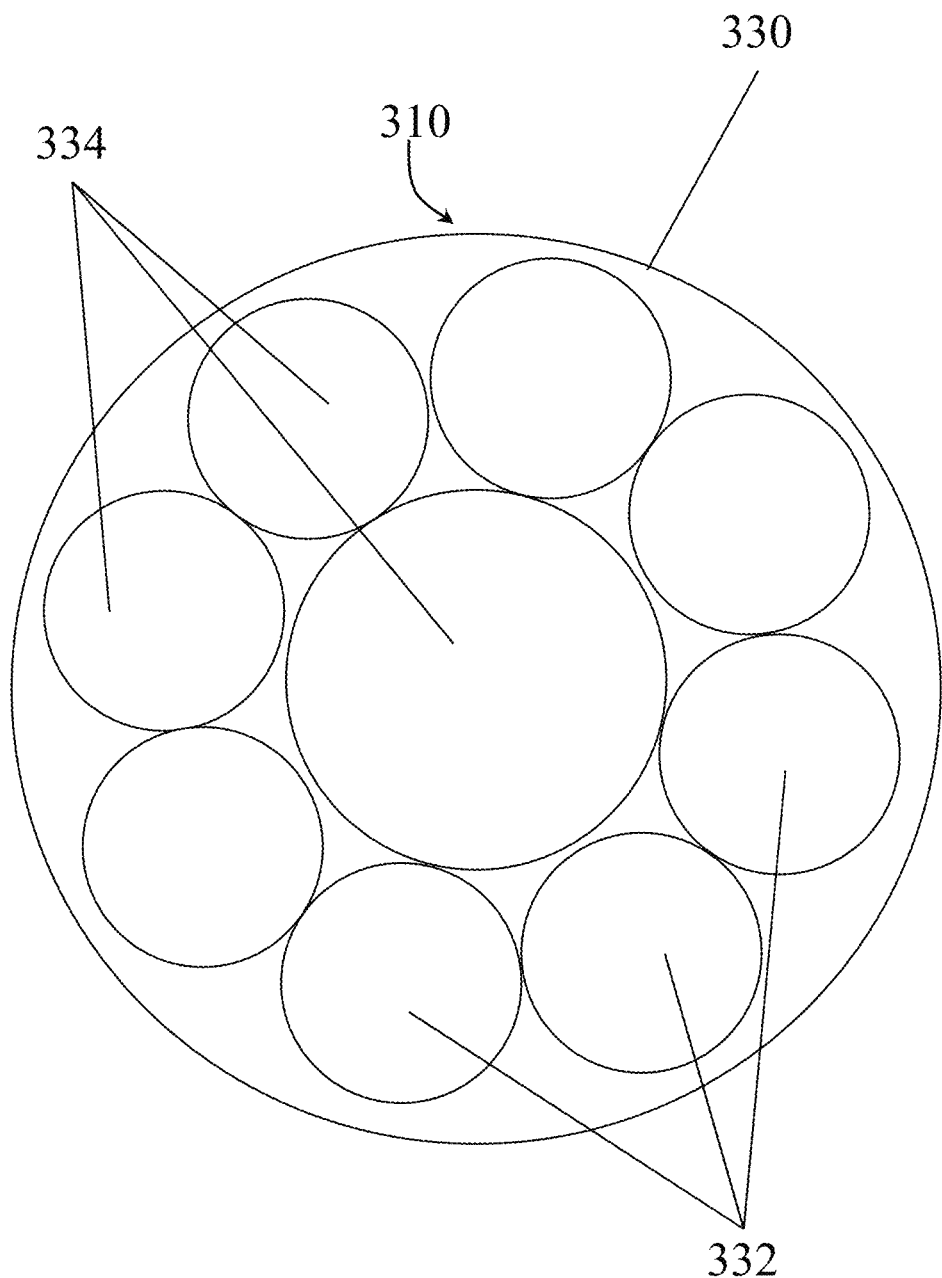

Referring to FIGS. 5A-5C, example cross-sectional views of the cabling 310 are depicted. In some embodiments, the cabling 310 can include a cable shielding 330 surrounding each of the components (e.g., the wiring 312 and the lumen 314) encased within the cabling 310. The cable shielding 330 can be designed to protect the inner components while remaining flexible. In some embodiments, the cable shielding 330 is shrink wrapped around the inner components for a tight-fitting structure, as depicted in FIG. 5A. In some embodiments, the cabling 310 can be constructed from a biocompatible material, such as, plastic material, elastomeric material, metallic material, shape memory material, composite material or any other materials that has the desired characteristics.

In some embodiments, the electrical wiring 312 made up of a combination of separate wires 332. The wires 332 can include any combination of power and/or signal transferring wires. The wires 332, as depicted in FIG. 5A, are wrapped within the cable shielding 330. The wires 332 can include any combination of bare conductive materials, insulated conductive materials, and shields conductive materials. In some embodiments, the wires 332 can be 24 AWG copper wires, each insulated with non-phthalate PVC with the size of the wires 332 and the insulation rated for 600V.

In some embodiments, the cabling 310 can include a conduit 334 for protecting the lumen 314 and to deliver a combination of gases and liquids to the device 100. The conduit 334 can be made from any combination of materials, for example an insulating material. The lumen 314 can be jacketed by a think paper to allow for flexibility of the cabling 310 without binding, and then wrapped again in a PVC or polyolefin jacket. Although only a single lumen 314 is depicted in FIG. 5A, any number of lumens can be used without departing from the scope of the present disclosure. In some embodiments, the conduit 334 can include one opening at a distal end thereof (i.e., from which the media is ejected/injected into the patient's body). In other embodiments, the conduit 334 include two or more openings at the distal end. The conduit 334 can be constructed from any combination of materials at desired levels of flexibility/rigidity. For example, the conduit 334 can be constructed from biocompatible materials (e.g., PVC, polyurethane, Tygon®, etc.). The conduit 334 or other surrounding for the lumens 314 can be sized at a dimension that is large enough to achieve the desired flow rates for the particular media being transferred therein, for example, the ID can be $\frac{1}{32}$"-$\frac{1}{4}$" ID. Similarly, the wall thickness of the conduit 334 or surrounding for a lumen 314 can depend on pressure requirements, for example, ranging from $\frac{1}{32}$-$\frac{1}{16}$ mm.

In some embodiments, the cabling 310 can be unshielded when there are not signal wires within the cabling 310, such as camera, imaging, data cables, etc. In contrast, the cabling 310 can be shielded if one or more of the wires 332 are designed to transmit a signal. The finished cabling 310, including a combination of wires 332 and lumens 314, can range in size depending on the respective sizes of the wires 332 and lumens 314 included therein. For example, when designed for use with a medical device (e.g., EVH device 100) the cabling 310 can be can be about 4 mm to 10 mm in diameter.

In some embodiments, the wires 332 can be spaced around a shielding 330 such that the shielding 330 forms a substantially circular cross section. In embodiments, to create a substantially circular cross section, spaces remaining between the conduit 334 and the wires 332 can be supplemented by spacers 336. Although the elements in FIG. 5A are substantially circular, any combination of shapes can be used without departing from the scope of the present invention.

Referring to FIG. 5B, in some embodiments, instead of integrating a conduit 334 within the cabling 310, the negative space between the shielding 330 and any wires 332 within the shielding 330 can constitute a pathway/cavity/space that is formed along the length of the cabling 310 to create a pathway 340 for the passage of the media along the length of the cabling 310 to the device 100. In some embodiments, this pathway 340 can be formed, for example, during the extrusion of the cabling 310. The shielding 330 (and components therein) can be constructed from any combination of materials with different rigidity levels, which can be selected based on desired form and function of the shielding 330. For example, the shielding 330 can be designed such that it maintains flexibly without kinking of the wiring 312, pathway 340, and/or media conduit 334 residing therein.

Referring to FIG. 5C, in some embodiments, the cabling 310 can include any combination of wires 332, conduits 334, etc. therein. For example, the cabling 310 can camera cables, light (e.g., fiber optic) cables, etc. Similarly, the cabling 310 can be designed for any combination of functions and provide certain utility to the attached device. For example, when designed for use with the EVH device 100, the cabling 310 can include a power cable for cautery, an insufflation lumen, an irrigation lumen (optional), camera power and signal cord wires, and scope light source wires or fiber optics. The cabling 310 of the present disclosure can incorporate any or all of those lines into a single cabling for ease of use and reduction of clutter for an operator. The components included within the cabling 310 can vary based on the device that the cabling 310 is designed to operate with. This is an improvement over conventional systems in which each function has its own separate cable and/or tube. For example, a separate power cord to deliver electricity, a separate insufflation tube to deliver media, a separate saline tube to deliver irrigation fluid, a separate light cable to deliver light to the scope, etc.

Figure 5D:
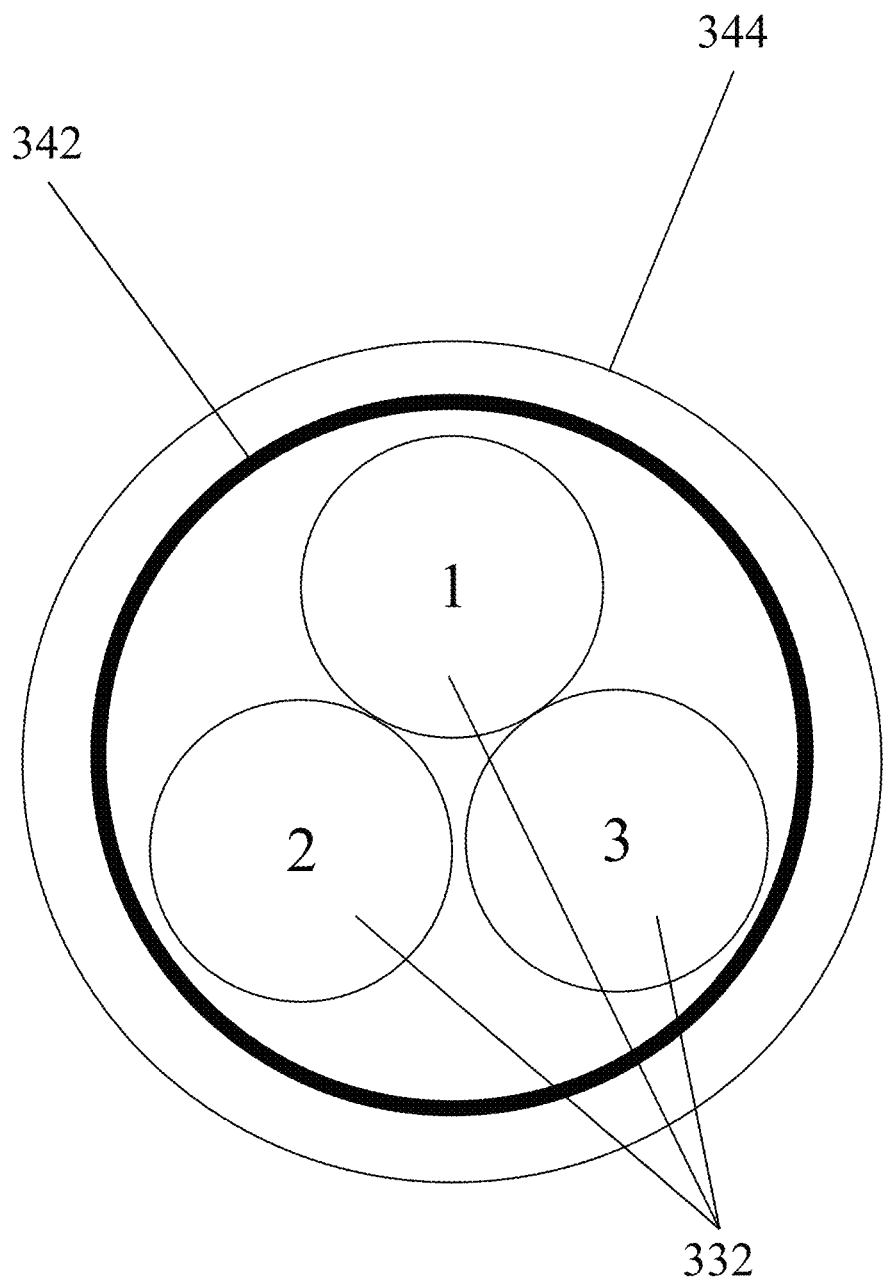

Referring to FIG. 5D, in some embodiments, the cabling 310 can include any combination of additional layers surrounding the wires 332 and lumens 314. For example, the wires 332 can be bundles together and surrounded by a paper tape layer 342 and a jacket layer 344.

In operation, an operator introduces the components of the system 300 into the sterile field within the OR, including the device 100 and the electrical wiring 312 and the lumen 314 included within the single cabling 310 structure. The operator can insert the connection points 322, 324 at the proximal end 320 of the cabling 310 into the appropriate devices. For example, the electrical plug 322 can be inserted into an electrical outlet (i.e., away from the sterile field/OR table), and the lumen connection 324 (e.g., insufflation conduit) can be connected to the OR media supply lumen (i.e., away from the sterile field/OR table). The operator can then initiate the desired procedure using the device 100. Upon activation of the device, the media can travel through the lumen 314, which is hidden from view (i.e., in the sterile field) and buried inside the cabling 310, to deliver media to the device 100 without requiring the operator to make any additional connections in the sterile field. This provides a cleaner, more elegant OR system 300, while maintaining the media delivery lumen. For example, the procedure can be an EVH procedure using an EVH device which can use an insufflation conduit (e.g., the lumen 314) to insufflate the leg (or other body part) of a patient as required while powering the device (e.g., the wiring 312).

In some embodiments, the length of cabling 310a can be substantially uniform in shape such that there are no points where either the electrical wires or the lumens change in materials or size. With this design the length of cabling 310a can be manufactured in continuous lengths and then cut to length. Thereafter, the end connectors (e.g., bifurcation 316 and strain relief 326) can be affixed to each end.

Although the present disclosure provides an example for using the cabling system 100 with an EVH device, the cabling system 100 of the present disclosure can be used with any combination of surgical or medical devices as well as non-surgical devices. In other words, the cabling can be used with any combination of devices that require one or more cables or lines attached to various machines. The cabling can be used with devices needing power, dispensing fluid, dispensing gases, imaging, illumination, heating or cooling, etc. For example, the cabling off the present disclosure can be used for a power drill to both power the drill and apply lubrication to cool the drill during operation. All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It will be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about", "generally", and "approximately" are intended to cover variations that may existing in the upper and lower limits of the ranges of subjective or objective values, such as variations in properties, parameters, sizes, and dimensions. In one non-limiting example, the terms "about", "generally", and "approximately" mean at, or plus 10 percent or less, or minus 10 percent or less. In one non-limiting example, the terms "about", "generally", and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present disclosure will be apparent to those skilled in the art in view of the foregoing description. Accordingly, this description is to be construed as illustrative only and is for the purpose of teaching those skilled in the art the best mode for carrying out the present disclosure. Details of the structure may vary substantially without departing from the spirit of the present disclosure, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present disclosure be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A cabling apparatus comprising:
    a flexible elongated body having a distal end to be coupled to a surgical device and an opposing proximal end;
    wiring extending at least partially within the elongated body along which data can be transmitted;
    a lumen extending at least partially within the elongated body through which media can be directed; and
    a bifurcated junction located at the proximal end of the elongated body having a first pathway extending from the junction to connect the wiring to a data source and a second pathway extending from the junction to connect the lumen to a media source positioned spatially away from the data source.

2. The apparatus of claim 1, further comprising an electrical plug coupled to a proximal end of the wiring.

3. The apparatus of claim 1, further comprising a lumen connection coupled to a proximal end of the lumen.

4. The apparatus of claim 1, further comprising a molded strain relief at a distal end of the cabling apparatus for coupling to a medical device.

5. The apparatus of claim 1, wherein the wiring comprises three wires.

6. The apparatus of claim 1, further comprising at least one spacer within the cabling.

7. The apparatus of claim 1, wherein the wiring transmits both power and data.

* * * * *